(12) United States Patent
Greenblatt et al.

(10) Patent No.: US 6,706,757 B2
(45) Date of Patent: Mar. 16, 2004

(54) CHROMAN DERIVATIVES AS 5-HYDROXYTRYPTAMINE-6 LIGANDS

(75) Inventors: Lynne Padilla Greenblatt, Lambertville, NJ (US); Michael Gerard Kelly, Thousand Oaks, CA (US)

(73) Assignee: Wyeth, Madison, NJ (US)

( * ) Notice: Subject to any disclaimer, the term of this patent is extended or adjusted under 35 U.S.C. 154(b) by 16 days.

(21) Appl. No.: 10/263,890

(22) Filed: Oct. 2, 2002

(65) Prior Publication Data

US 2003/0158175 A1 Aug. 21, 2003

Related U.S. Application Data

(60) Provisional application No. 60/326,957, filed on Oct. 4, 2001.

(51) Int. Cl.[7] ............... A61K 31/35; A61K 31/44; C07D 405/00; C07D 271/12; C07D 417/02
(52) U.S. Cl. ............... 514/456; 514/457; 514/458; 514/337; 514/314; 549/398; 549/404; 549/408; 549/60; 549/58; 546/283.1; 548/126; 548/146; 544/62
(58) Field of Search ............... 514/456, 457, 514/458, 337, 314; 549/398, 404, 408, 60, 58; 546/283.1; 548/126, 146; 544/62

(56) References Cited

U.S. PATENT DOCUMENTS

| 5,663,194 | A |   | 9/1997  | Mewshaw         |         |
|-----------|---|---|---------|-----------------|---------|
| 5,824,682 | A |   | 10/1998 | Van Lommen et al.|        |
| 5,962,513 | A |   | 10/1999 | Schohe-Loop et al.|       |
| 5,977,167 | A | * | 11/1999 | Koga et al.     | 514/456 |
| 6,034,256 | A | * | 3/2000  | Carter et al.   | 549/456 |
| 6,051,586 | A | * | 4/2000  | Ladouceur et al.| 514/337 |
| 6,060,506 | A | * | 5/2000  | Catt et al.     | 514/450 |
| 6,071,938 | A | * | 6/2000  | MacKenzie et al.| 514/337 |
| 6,191,164 | B1| * | 2/2001  | Lang et al.     | 514/456 |
| 6,323,238 | B1| * | 11/2001 | Yoo et al.      | 514/456 |
| 6,395,909 | B1| * | 5/2002  | Bell et al.     | 549/404 |
| 6,417,223 | B1| * | 7/2002  | Sanders et al.  | 514/456 |
| 6,448,269 | B1| * | 9/2002  | Fisher et al.   | 514/320 |
| 6,589,983 | B1| * | 7/2003  | Tanikawa et al. | 514/456 |
| 6,596,758 | B1| * | 7/2003  | Brunet et al.   | 514/450 |
| 6,599,918 | B2| * | 7/2003  | Burns et al.    | 514/314 |

FOREIGN PATENT DOCUMENTS

| WO | WO 99/32475 A1 | 7/1999  |
|----|----------------|---------|
| WO | WO 00/76990 A1 | 12/2000 |

OTHER PUBLICATIONS

Mewshaw, R. E., et al, Journal of Medicinal Chemistry, 1997, 40, 4235–4256.
Boess, F. G., et al, Molecular Pharmacology, 1998, 54, 577–583.

\* cited by examiner

Primary Examiner—Deborah C Lambkin
(74) Attorney, Agent, or Firm—Barbara L. Lences

(57) ABSTRACT

The present invention provides a compound of formula I and the use thereof for the therapeutic treatment of disorders relating to or affected by the 5-HT6 receptor.

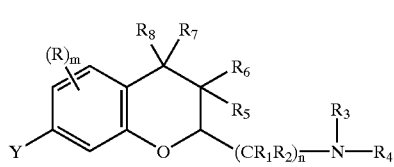

(I)

20 Claims, No Drawings

CHROMAN DERIVATIVES AS 5-HYDROXYTRYPTAMINE-6 LIGANDS

BACKGROUND OF THE INVENTION

This application claims priority from copending provisional application Ser. No. 60/326957, filed on Oct. 4, 2001, the entire disclosure of which is hereby incorporated by reference.

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex.

Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorders, attention deficit disorder, migraine, cognitive memory enhancement (e.g. for the treatment of Alzheimer's disease), sleep disorders, feeding disorders (e.g. anorexia and bulimia), panic attacks, withdrawal from drug abuse (e.g. cocaine, ethanol, nicotine and benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a chroman compound of formula I

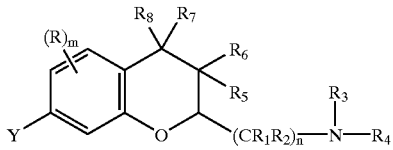

wherein
Y is $SO_2NR_9R_{10}$ or $NR_{11}ZR_{12}$;
Z is $SO_2$, CONH or CSNH;
R is halogen, CN, $OR_{13}$, $CO_2R_{14}$, $CONR_{15}R_{16}$, $SO_xR_{17}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_1$, $R_2$, $R_5$, $R_6$, $R_7$, $R_8$ and $R_{11}$ are each independently H or an optionally substituted $C_1$–$C_6$alkyl group;
$R_3$ and $R_4$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1$–$C_6$alky or aryl group then $R_3$ and $R_4$ must be other than an optionally substituted $C_3$–$C_6$cycloalkyl or cycloheteroalkyl group;
m is 0 or an integer of 1, 2 or 3;
n is an integer of 1, 2, 3 or 4;
x is 0 or an integer of 1 or 2;
$R_9$ and $R_{10}$ are each independently H or a $C_1$–$C_6$alkyl, aryl or heteroaryl group each optionally substituted;
$R_{12}$ and $R_{17}$ are each independently a $C_1$–$C_6$alkyl, aryl or heteroaryl group each optionally substituted;
$R_{13}$ is H, $CO_2R_{18}$ or a $C_1$–$C_6$alkyl, $C_2$–$C_6$alkenyl, $C_2$–$C_6$alkynyl, aryl or heteroaryl group each optionally substituted;
$R_{14}$ and $R_{18}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and
$R_{15}$ and $R_{16}$ are each independently H or an optionally substituted $C_1$–$C_6$alkyl group; or
the stereoisomers thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that chroman derivatives of formula I demonstrate 5-HT6 affinity. Advantageously, said chroman derivatives may be used as effective therapeutic agents for the treatment of central nervous system (CNS) disorders associated with or affected by the 5-HT6 receptor. Accordingly, the present invention provides chroman derivatives of formula I

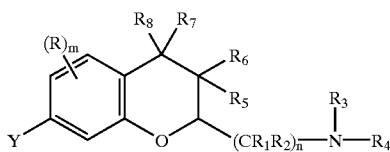

(I)

wherein
Y is $SO_2NR_9R_{10}$ or $NR_{11}ZR_{12}$;
Z is $SO_2$, CONH or CSNH;
R is halogen, CN, $OR_{13}$, $CO_2R_{14}$, $CONR_{15}R_{16}$, $SO_xR_{17}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_1$, $R_2$, $R_5$, $R_6$, $R_7$, $R_8$ and $R_{11}$ are each independently H or an optionally substituted $C_1$–$C_6$alkyl group;
$R_3$ and $R_4$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1$–$C_6$alky or aryl group then $R_3$ and $R_4$ must be other than an optionally substituted $C_3$–$C_6$cycloalkyl or cycloheteroalkyl group;
m is 0 or an integer of 1, 2 or 3;
n is an integer of 1, 2, 3 or 4;
x is 0 or an integer of 1 or 2;
$R_9$ and $R_{10}$ are each independently H or a $C_1$–$C_6$alkyl, aryl or heteroaryl group each optionally substituted;
$R_{12}$ and $R_{17}$ are each independently a $C_1$–$C_6$alkyl, aryl or heteroaryl group each optionally substituted;
$R_{13}$ is H, $CO_2R_{18}$ or a $C_1$–$C_6$alkyl, $C_2$–$C_6$alkenyl, $C_2$–$C_6$alkynyl, aryl or heteroaryl group each optionally substituted;
$R_{14}$ and $R_{18}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and
$R_{15}$ and $R_{16}$ are each independently H or an optionally substituted $C_1$–$C_6$alkyl group; or
the stereoisomers thereof or a pharmaceutically acceptable salt thereof.

The present invention also provides methods and compositions useful for the therapeutic treatment of central nervous system disorders related to or affected by the 5-HT6 receptor.

As used in the specification and claims, the term halogen designates Br, Cl, I or F and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S.

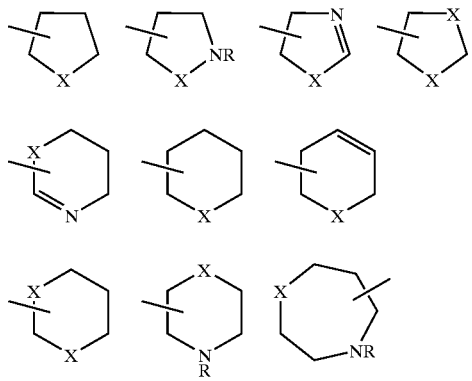

Similarly, as used in the specification and claims, the term heteroaryl designates a $C_5$–$C_{10}$ aromatic ring system containing 1 or 2 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, phenyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein Z is $SO_2$. Also preferred are those compounds of formula I wherein $R_{10}$ and $R_{12}$ are each independently an aryl or heteroaryl group each optionally substituted. Another group of preferred compounds of formula I are those compounds wherein n is 1 and m is 0.

More preferred compounds of the invention are those compounds of formula I wherein Z is $SO_2$ and $R_{10}$ and $R_{12}$ are each independently an aryl or heteroaryl group each optionally substituted. Another group of more preferred compounds of the invention are those compounds of formula I wherein Y is $NR_{11}ZR_{12}$; Z is $SO_2$; n is 1; and m is 0. Further more preferred compounds of formula I are those compounds wherein Z is $SO_2$; $R_5$, $R_6$, $R_7$ and $R_8$ are H; and $R_{11}$ is H or $CH_3$.

Among the preferred compounds of the invention are:

N-{2-[(3-Hydroxy-propylamino)-methyl]-chroman-7-yl}-benzenesulfonamide;
N-(2-{[(3-methoxybenzyl)amino]methyl}-3,4-dihydro-2H-chromen-7-yl)benzenesulfonamide;
N-(2-{[(3-butoxypropyl)amino]methyl}-3,4-dihydro-2H-chromen-7-yl)benzenesulfonamide;
N-{2-[(benzylamino)methyl]-3,4-dihydro-2H-chromen-7-yl}benzenesulfonamide;
N-(2-{[(3-phenoxypropyl)amino]methyl}-3,4-dihydro-2H-chromen-7-yl)benzenesulfonamide;
N-[2-({[(1R)-1-phenylethyl]amino}methyl)-3,4-dihydro-2H-chromen-7-yl]benzenesulfonamide;
N-(2-{[(1,3-benzodioxol-5-ylmethyl)amino]methyl}-3,4-dihydro-2H-chromen-7-yl)benzenesulfonamide;
N-(2-{[(pyridin-3-ylmethyl)amino]methyl}-3,4-dihydro-2H-chromen-7-yl)benzenesulfonamide;
N-{2-[(2,3-dihydro-1H-inden-1-ylamino)methyl]-3,4-dihydro-2H-chromen-7-yl}benzenesulfonamide;
N-[2-({[(1S)-1-phenylethyl]amino}methyl)-3,4-dihydro-2H-chromen-7-yl]benzenesulfonamide;
N-(2-{[(pyridin-4-ylmethyl)amino]methyl}-3,4-dihydro-2H-chromen-7-yl)benzenesulfonamide;
N-[2-({[(1R)-2-hydroxy-1-phenylethyl]amino}methyl)-3,4-dihydro-2H-chromen-7-yl]benzenesulfonamide;
N-(2-{[(1,2-diphenylethyl)amino]methyl}-3,4-dihydro-2H-chromen-7-yl)benzenesulfonamide;
N-(2-{[(2-hydroxy-1,1-dimethylethyl)amino]methyl}-3,4-dihydro-2H-chromen-7-yl)benzenesulfonamide;
N-{2-[(isopropylamino)methyl]-3,4-dihydro-2H-chromen-7-yl}benzenesulfonamide;
N-(2-{[(1-methyl-3-phenylpropyl)amino]methyl}-3,4-dihydro-2H-chromen-7-yl)benzenesulfonamide;
N-(2-{[(1,5-dimethylhexyl)amino]methyl}-3,4-dihydro-2H-chromen-7-yl)benzenesulfonamide;
N-[2-({[(1R)-1-(hydroxymethyl)-3-methylbutyl]amino}methyl)-3,4-dihydro-2H-chromen-7yl]benzenesulfonamide;
N-(2-{[2-(2-hydroxyethyl)piperidin-1-yl]methyl}-3,4-dihydro-2H-chromen-7-yl)benzenesulfonamide;
N-{2-[(2,6-dimethylpiperidin-1-yl)methyl]-3,4-dihydro-2H-chromen-7-yl}benzenesulfonamide;
N-[2-(morpholin-4-ylmethyl)-3,4-dihydro-2H-chromen-7-yl]benzenesulfonamide;
N-[2-(thiomorpholin-4-ylmethyl)-3,4-dihydro-2H-chromen-7-yl]benzenesulfonamide;
N-[2-({[(1R)-1-cyclohexylethyl]amino}methyl)-3,4-dihydro-2H-chromen-7-yl]benzenesulfonamide;
N-(2-{[(3-hydroxypropyl)amino]methyl}-3,4-dihydro-2H-chromen-7-yl)naphthalene-2-sulfonamide;
N-(2-{[(3-hydroxypropyl)amino]methyl}-3,4-dihydro-2H-chromen-7-yl)-4-methoxybenzenesulfonamide;
4-fluoro-N-(2-{[(3-hydroxypropyl)amino]methyl}-3,4-dihydro-2H-chromen-7-yl)benzenesulfonamide;
4-chloro-N-(2-{[(3-hydroxypropyl)amino]methyl}-3,4-dihydro-2H-chromen-7-yl)benzenesulfonamide;
N-[2-({[(1R)-1-phenylethyl]amino}methyl)-3,4-dihydro-2H-chromen-7-yl]-2,1,3-benzoxadiazole-4-sulfonamide;
6-chloro-N-[2-({[(1R)-1-phenylethyl]amino}methyl)-3,4-dihydro-2H-chromen-7-yl]imidazo[2,1-b][1,3]thiazole-5-sulfonamide;
5-bromo-N-[2-({[(1R)-1-phenylethyl]amino}methyl)-3,4-dihydro-2H-chromen-7-yl]-2-thiophenesulfonamide;
N-[4-methyl-5-({[2-({[(1R)-1-phenylethyl]amino}methyl)-3,4-dihydro-2H-chromen-7-yl]amino}sulfonyl)-1,3-thiazol-2-yl]acetamide;
5-chloro-3-methyl-N-[2-({[(1R)-1-phenylethyl]amino}methyl)-3,4-dihydro-2H-chromen-7-yl]-1-benzothiophene-2-sulfonamide;
N-[(2R)-2-({[(1R)-1-phenylethyl]amino}methyl)-3,4-dihydro-2H-chromen-7-yl]benzenesulfonamide;
N-[(2S)-2-({[(1R)-1-phenylethyl]amino}methyl)-3,4-dihydro-2H-chromen-7-yl]benzenesulfonamide;
4-methyl-N-[2-({[(1R)-1-phenylethyl]amino}methyl)-3,4-dihydro-2H-chromen-7-yl]benzenesulfonamide;
4-chloro-N-[2-({[(1R)-1-phenylethyl]amino}methyl)-3,4-dihydro-2H-chromen-7-yl]benzenesulfonamide;
4-methoxy-N-[2-({[(1R)-1-phenylethyl]amino}methyl)-3,4-dihydro-2H-chromen-7-yl]benzenesulfonamide;
N-[2-({[(1R)-1-phenylethyl]amino}methyl)-3,4-dihydro-2H-chromen-7-yl]-4-(trifluoromethoxy)benzenesulfonamide;
N-[2-({[(1R)-1-phenylethyl]amino}methyl)-3,4-dihydro-2H-chromen-7-yl]naphthalene-1-sulfonamide;
5-chloro-N-[2-({[(1R)-1-phenylethyl]amino}methyl)-3,4-dihydro-2H-chromen-7-yl]thiophene-2-sulfonamide;
N-[2-({[(1R)-1-phenylethyl]amino}methyl)-3,4-dihydro-2H-chromen-7-yl]-4-(trifluoromethyl)benzenesulfonamide;
5-chloro-N-methyl-N-[2-({[(1R)-1-phenylethyl]amino}methyl)-3,4-dihydro-2H-chromen-7-yl]thiophene-2-sulfonamide;
4-amino-N-[2-({[(1R)-1-phenylethyl]amino}methyl)-3,4-dihydro-2H-chromen-7-yl]benzenesulfonamide;
2-bromo-N-methyl-N-[2-({[(1R)-1-phenylethyl]amino}methyl)-3,4-dihydro-2H-chromen-7-yl]benzenesulfonamide;
4-fluoro-N-methyl-N-[2-({[(1R)-1-phenylethyl]amino}methyl)-3,4-dihydro-2H-chromen-7-yl]benzenesulfonamide;
4-chloro-N-methyl-N-[2-({[(1R)-1-phenylethyl]amino}methyl)-3,4-dihydro-2H-chromen-7-yl]benzenesulfonamide;
3,4-dimethoxy-N-methyl-N-[2-({[(1R)-1-phenylethyl]amino}methyl)-3,4-dihydro-2H-chromen-7-yl]benzenesulfonamide;

N-methyl-N-[2-({[(1R)-1-phenylethyl]amino}methyl)-3,4-dihydro-2H-chromen-7-yl]naphthalene-1-sulfonamide;
4-amino-N-methyl-N-[2-({[(1R)-1-phenylethyl]amino}methyl)-3,4-dihydro-2H-chromen-7-yl]benzenesulfonamide;
N-[(2R)-2-({[(1R)-1-phenylethyl]amino}methyl)-3,4-dihydro-2H-chromen-7-yl]naphthalene-1-sulfonamide;
3N-[(2S)-2-({[(1R)-1-phenylethyl]amino}methyl)-3,4-dihydro-2H-chromen-7-yl]naphthalene-1-sulfonamide;
4-amino-N-[(2R)-2-({[(1R)-1-phenylethyl]amino}methyl)-3,4-dihydro-2H-chromen-7-yl]benzenesulfonamide;
4-amino-N-[(2S)-2-({[(1R)-1-phenylethyl]amino}methyl)-3,4-dihydro-2H-chromen-7-yl]benzenesulfonamide; or the stereoisomers thereof and the pharmaceutically acceptable salts thereof.

Compounds of the invention may be prepared using conventional synthetic methods and, if required, standard separation and isolation techniques. For example, compounds of formula I wherein Y is $NR_{11}ZR_{12}$; Z is $SO_2$; and $R_{11}$ is H (Ia) may be prepared from the appropriately substituted 7-amino-2-(hydroxyalkyl)chroman of formula II by reacting said formula II chroman with a sulfonyl halide, $R_{12}Z$-Hal to give the intermediate of formula III and reacting said formula III intermediate with an amine, $HNR_3R_4$, to give the desired compound of formula Ia. The reaction is shown in flow diagram I wherein Hal is Cl, Br or I.

Flow Diagram I

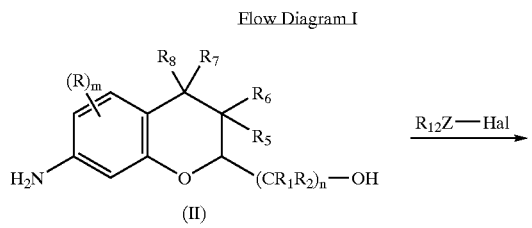

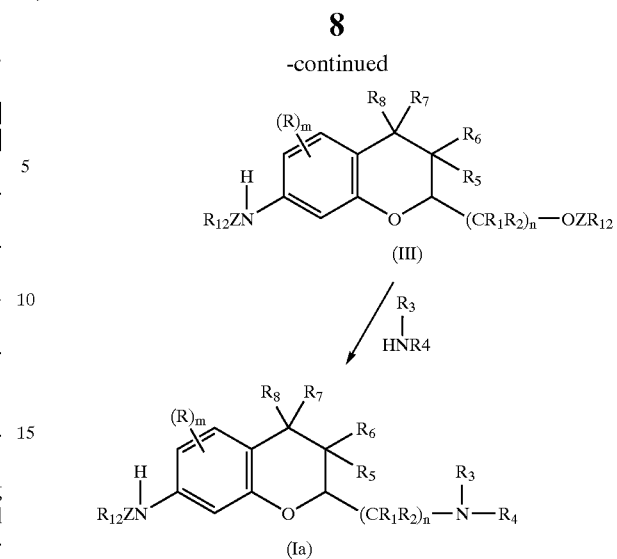

Compounds of formula I wherein Y is $SO_2NR_9R_{10}$ (Ib) may be prepared by reacting a 7-amino-2-(hydroxyalkyl)chroman of formula II with sodium nitrite to form the corresponding 7-diazo intermediate; displacing the diazo group with $SO_2$ in the presence of $CuCl_2$ to give the sulfonyl chloride of formula IV; reacting said formula IV sulfonyl chloride with an amine, $HNR_9R_{10}$ to give the corresponding chromansulfonamide of formula V; activating the hydroxy moiety of the formula V compound with p-toluenesulfonyl chloride to give the compound of formula VI; and displacing the O-tosyl group with an amine, $HNR_3R_4$. The reaction sequence is shown in flow diagram II wherein p-tsCl represents p-toluenesulfonyl chloride.

Flow Diagram II

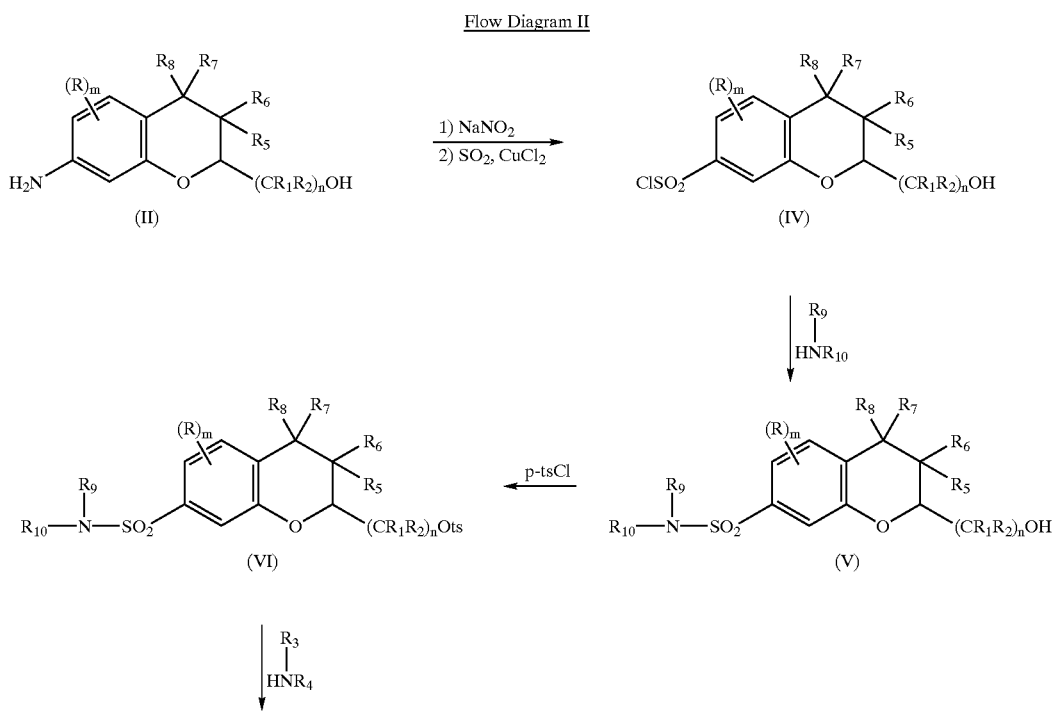

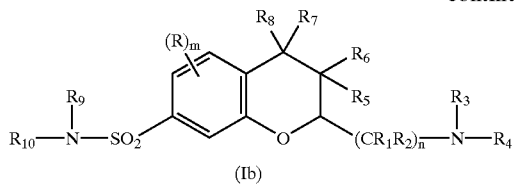

(Ib)

Compounds of formula I wherein Y is $NR_{11}ZR_{12}$ and Z is CONH or CSNH (Ic) may be prepared by reacting a compound of formula II with the appropriate acyl or thionyl halide to give the intermediate compound of formula VII; activating the hydroxy moiety of the formula VII compound with p-toluenesulfonyl chloride and subsequently displacing the O-tosyl group with an amine, $HNR_3R_4$. The reaction sequence is shown in flow diagram III wherein Z' represents CONH or CSNH; and the terms Hal and p-tsCl are defined hereinabove.

Flow Diagram III

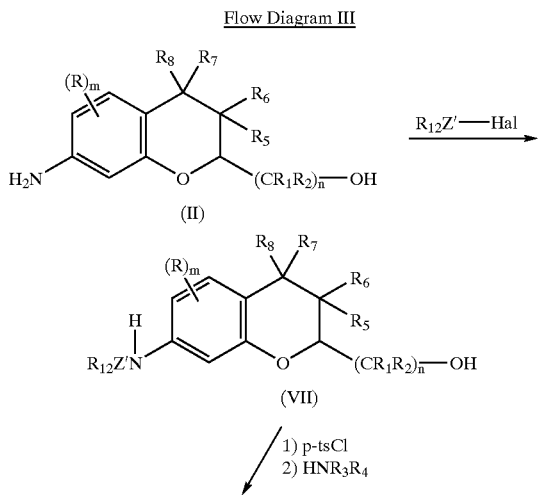

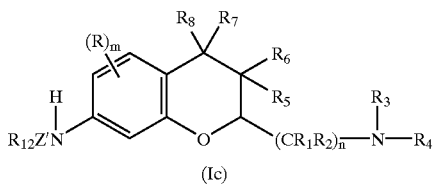

(Ic)

Compounds of formula II wherein n is 1 and $R_1$ and $R_2$ are H (IIa) may be prepared by O-acetylating a 3-acetamidophenol of formula VIII to give the diacetylated compound of formula IX; subjecting said formula IX compound to a Fries rearrangement to form the 4-acetamido-2-hydroxyacetophenone of formula X; reacting the formula X compound with diethyl oxalate to give the 7-amino-4-oxo-4H-1-benzopyran-2-carboxylate of formula XI; reducing the formula XI compound via catalytic hydrogenation to give the 7-aminochroman ester of formula XII; and further reducing said formula XII ester to give the desired 7-amino-2-(hydroxymethyl)chroman of formula IIa. The reaction sequence is illustrated in flow diagram IV wherein Et represents a $C_2H_5$ group.

Flow Diagram IV

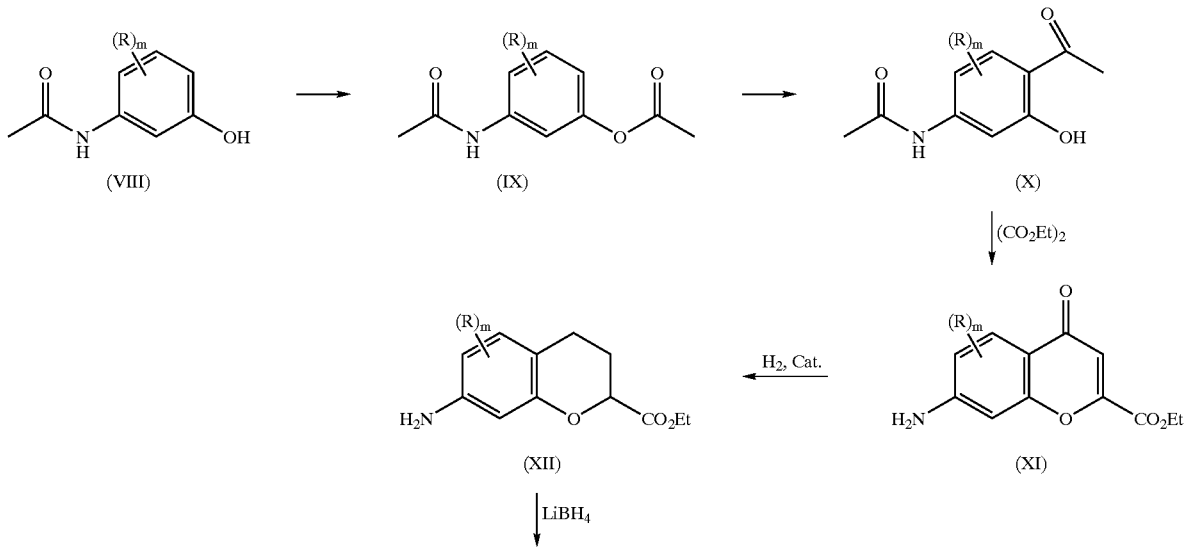

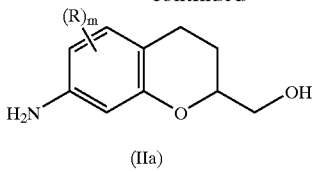

(IIa)

Using these and other conventional methods, compounds of formula I may be prepared from readily available starting materials.

The present invention also provides a convenient and effective process for the preparation of a compound of formula I which comprises reacting a compound of formula XIII

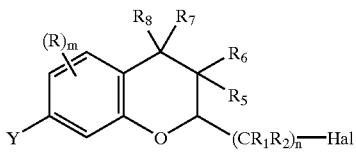

wherein Y, m, n, R, $R_1$, $R_2$, $R_5$, $R_6$, $R_7$ and $R_8$ are as defined for formula I and Hal is Cl, Br or I with an amine, $HNR_3R_4$, at an elevated temperature optionally in the presence of a solvent to give the desired formula I product. The process is illustrated in flow diagram V.

Flow Diagram V

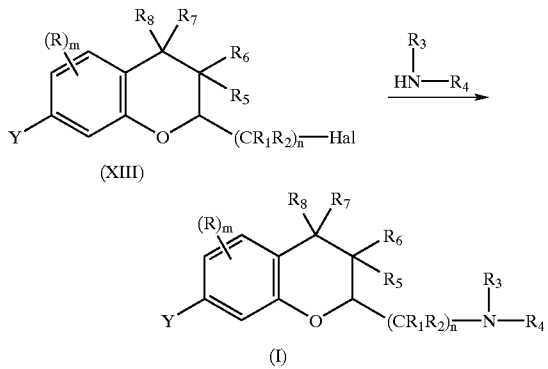

Elevated reaction temperatures suitable for use in the process of the invention range from about 30° C. to the reflux temperature of the solvent or the amine, $HNR_3R_4$.

Suitable solvents include any non-reactive conventional solvent such as acetonitrile, ethyl acetate, diethyl ether, tetrahydrofuran, methylene chloride, toluene, dihalobenzene, dimethylsulfoxide, dimethyl formamide, or the like.

Advantageously, the inventive compound of formula I may be utilized in the treatment of central nervous system disorders relating to or affected by the 5-HT6 receptor such as motor, mood, psychiatric, cognitive, neurodegenerative, or the like disorders; for example, Alzheimer's disease, Parkinson's disease, attention deficit disorder, anxiety, epilepsy, depression, obsessive compulsive disorder, migraine, sleep disorders, feeding disorders (such as anorexia or bulimia), schizophrenia, memory loss, disorders associated with withdrawl from drug abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmoregulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms NMR and HPLC designate nuclear magnetic resonance and high performance liquid chromatography, respectively. The term THF designates tetrahydrofuran.

EXAMPLE 1

Preparation of Ethyl 7-Amino-4-oxo-4H-chromene-2-carboxylate

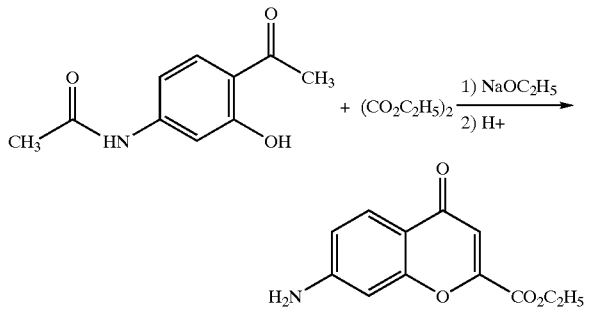

A solution of N-(4-acetyl-3-hydroxyphenyl)acetamide (4.00 g., 21 mmol) and diethyl oxalate (7.3 mL, 54 mmol) in absolute ethanol is added dropwise to a solution of sodium ethoxide (0.1 mol) in absolute ethanol. The mixture is heated at reflux temperature for 1.5 h, cooled to ambient temperature, poured into water, acidified to pH 3 with 6N HCl and extracted with ethyl acetate. The extracts are combined and concentrated in vacuo to afford an oily residue. The residue is dissolved in ethanol, treated with concentrated HCl heated at reflux temperature overnight, cooled to 0° C. for several hours and filtered. The filtercake is dried to afford the title compound as an orange solid, 2.95 g (61% yield), mp 195°–198° C., identified by NMR and mass spectral analyses.

EXAMPLE 2

Preparation of Ethyl 7-Amino-2-chromancarboxylate

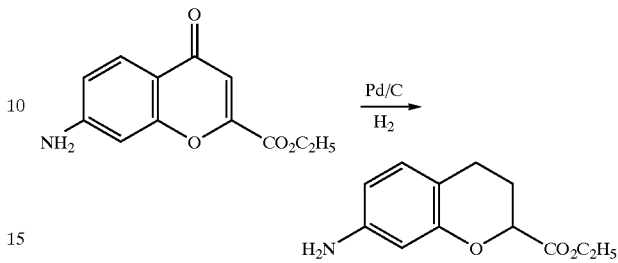

A solution of ethyl 7-amino-4-oxo-4H-chromene-2-carboxylate (1.00 g, 4.3 mmol) in ethanol and concentrated HCl (5 mL) is hydrogenated over 10% Pd/C (0.5 g) at 50 psi for 72 h at ambient temperature. The reaction mixture is filtered and the filtrate is concentrated in vacuo. The resultant residue is dissolved in ethyl acetate and washed with saturated aqueous $NaHCO_3$. The organic phase is dried over $MgSO_4$, and concentrated in vacuo to afford the title compound as an amber oil, 0.85 g (89% yield), identified by NMR and mass spectral analyses.

EXAMPLE 3

Preparation of 7-Amino-2-(hydroxymethyl)chroman

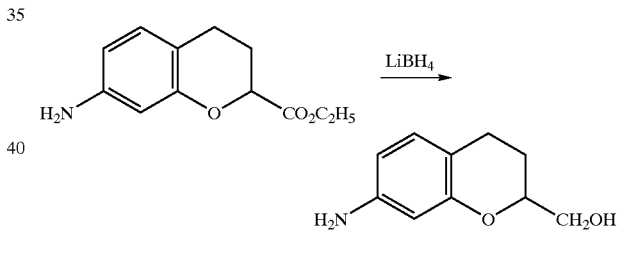

A solution of ethyl 7-amino-2-chromancarboxylate (1.26 g, 5.7 mmol) in anhydrous THF is treated dropwise with lithium borohydride (2.0 M in THF, 13.7 mmol), stirred under nitrogen at ambient temperatures for 4 h, quenched with methanol, stirred at ambient temperatures for 1 h, poured into water, extracted with ethyl acetate. The extracts are combined, dried over $MgSO_4$ and concentrated in vacuo to afford the title compound as a nearly colorless oil, 0.9 g (90% yield), identified by NMR and mass spectral analyses.

EXAMPLE 4

Preparation of {7-[(Phenylsulfonyl)amino]-3,4-dihydro-2H-chromen-2-yl}methylbenzenesulfonate

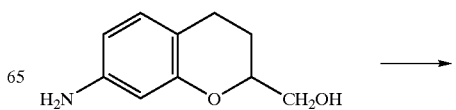

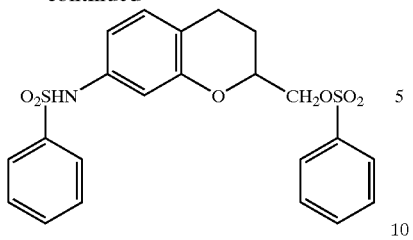

A solution of (7-amino-2-(hydroxymethyl)chroman (0.52 g, 2.9 mmol) in pyridine is treated with a solution of phenylsulfonyl chloride (0.81 mL, 6.4 mmol) in pyridine, stirred at ambient temperature for 1 h, poured into water and extracted with ethyl acetate. The extracts are combined, washed with brine, dried over $MgSO_4$ and concentrated in vacuo. The resultant residue is chromatographed (silica gel, ethyl acetate:hexane 1:1) to afford the title product as an off-white solid, 1.23 g (92% yield), identified by NMR and mass spectral analyses.

EXAMPLE 5

Preparation of N-{2-[(3-Hydroxypropylamino)methyl]chroman-7-yl}benzenesulfonamide Hemifumarate salt

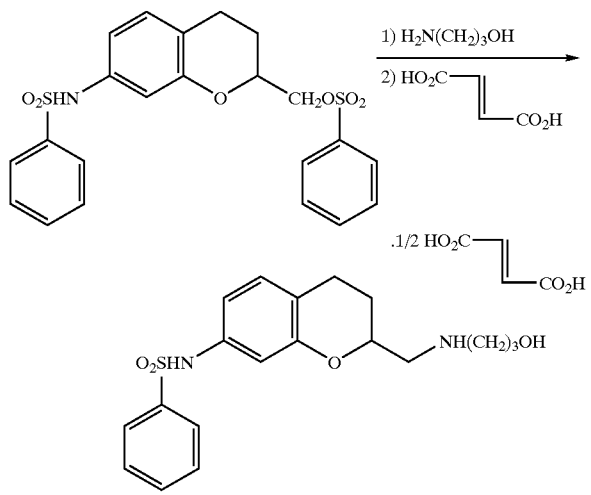

A solution of 2-(phenylsulfonyloxymethyl)-7-(phenylsulfonamide)chroman (0.59 g, 1.2 mmol and 3-amino-1-propanol (0.92 mL, 12 mmol) in pyridine is stirred at 100° C. for 1 h, cooled to ambient temperatures, diluted with water and extracted with methylene chloride. The extracts are combined, washed with brine, dried over $MgSO_4$ and concentrated in vacuo. The resultant residue is treated with an ethanolic solution of fumaric acid, cooled to 0° C. and filtered. The filtercake is dried to afford the title product as an off-white solid, 0.054 g, mp 195–197° C., identified by NMR and mass spectral analyses.

EXAMPLES 6–30

Preparation of 2-(Substituted-amino)-7-(phenylsulfonamido)chroman

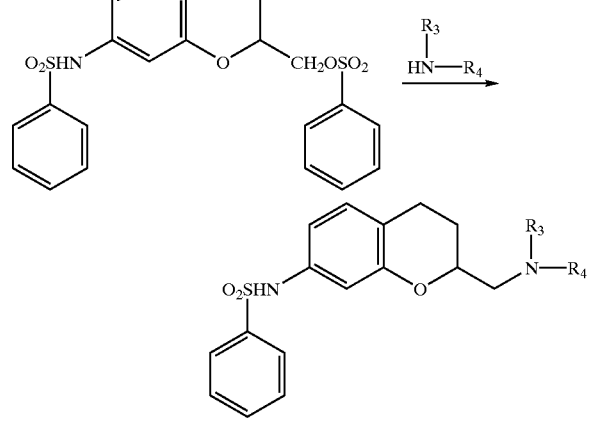

Using essentially the same procedure described in Example 5 hereinabove and employing the appropriate amine, the compounds shown in Table I are obtained and identified by HPLC and mass spectral analyses (LCMS).

TABLE I

| Example No. | R3 | R4 | LCMS[1] (M + H) | min. |
|---|---|---|---|---|
| 6 | H | 3-$CH_3OC_6H_4CH_2$— | 439 | 3.96 |
| 7 | H | $nC_4H_9OCH_2CH_2CH_2$— | 433 | 8.79 |
| 8 | H | $C_6H_5CH_2$— | 409 | 8.18 |
| 9 | H | $C_6H_5OCH_2CH_2CH_2$— | 453 | 9.18 |
| 10 | H | 1(R)-$C_6H_5CH(CH_3)$— | 423 | 8.57 |
| 11 | H | 1,3-benzodioxol-5-ylmethyl | 453 | 8.38 |
| 12 | H | pyridin-3-ylmethyl | 410 | 6.07 |
| 13 | H | 2,3-dihydro-1H-inden-1-yl | 435 | 8.86 |
| 14 | H | 1(S)-$C_6H_5CH(CH_3)$— | 423 | 8.76 |
| 15 | H | pyridin-4-ylmethyl | 410 | 5.44 |
| 16 | H | 1(R)-$C_6H_5CH(CH_2OH)$— | 439 | 8.14 |
| 17 | H | $C_6H_5CH_2CH(C_6H_5)$— | 499 | 10.16 |
| 18 | H | $(CH_3)_2CH(CH_2OH)$— | 391 | 5.90 |
| 19 | H | $(CH_3)_2CH$— | 361 | 6.14 |
| 20 | H | $C_6H_5CH_2CH_2CH(CH_3)$— | 451 | 8.41 |
| 21 | H | 1,5-dimethylhexyl | 431 | 8.85 |
| 22 | H | 1-(R)-$(CH_3)_2CH$—$CH_2CH(CH_2OH)$— | 419 | 7.17 |
| 23 | —$CH(C_2H_4OH)CH_2CH_2CH_2CH_2$— | | 431 | 6.31 |
| 24 | —$CH(CH_3)CH_2CH_2CH_2CH(CH_3)$— | | 415 | 7.19 |
| 25 | —$CH_2$—$CH_2$—O—$CH_2$—$CH_2$— | | 389 | 5.75 |
| 26 | —$CH_2$—$CH_2$—S—$CH_2$—$CH_2$— | | 405 | 6.33 |
| 27 | H | 1(R)-1-cyclohexylethyl | 429 | 8.32 |

[1]LCMS conditions: Hewlett Packard 1100 MSD; Primesphere C18 2.0 mm × 150 mm, 5μ; column at 35° C., 2 μL injection; Solvent A: 0.1% HCOOH/water; Solvent B: 0.1% HCOOH/acetonitrile; Gradient: Time 0 min.: 0% B; 8.5 min.: 100% B; 8.6 min: 0% B; Equilibration: 4 min, 20% B; Flow rate 0.5 mL/min; Detection: 254 nm DAD; API-ES Scanning Mode Positive 100–1000; Fragmentor 80 mV.

EXAMPLE 28

Preparation of N-(2-{[(3-Hydroxypropyl)amino]methyl}-3,4-dihydro-2H-chromen-7-yl)naphthalene-2-sulfonamide

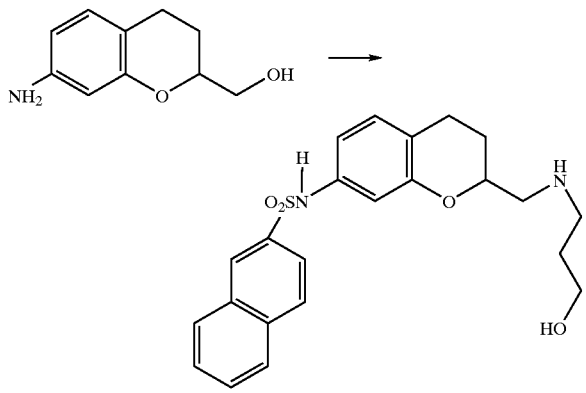

A solution of (7-amino-3,4-dihydro-2H-chromen-2-yl)methanol (25 mg, 140 μmol) in pyridine is treated with 2-naphthalenesulfonylchloride (70 mg, 308 μmol) at ambient temperature for 1 h, treated with 3-amino-1-propanol (3 mmol, 0.23 mL), heated at 80° C. for 3 h, diluted with water and extracted with ethyl acetate. The extracts are combined, dried over $Na_2SO_4$ and concentrated in vacuo. The resultant residue is purified by reverse phase preparative HPLC to give the title product, M+H 427, retention time 7.92 min.

EXAMPLES 29–31

Preparation of [(3-Hydroxypropyl)aminomethyl-chroman-7-yl]arylsulfonamide

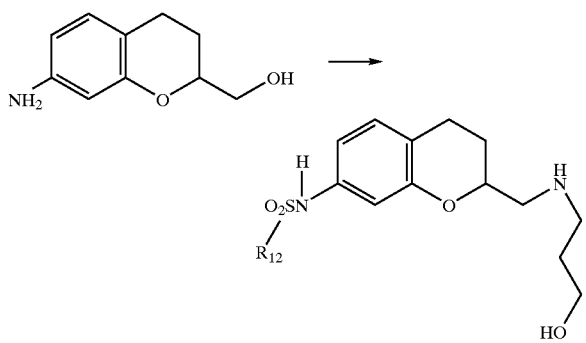

Using essentially the same procedure described in Example 28, hereinabove and substituting the appropriate arylsulfonyl chloride, the compounds shown in Table III are obtained and identified by mass spectral and HPLC analyses (LCMS).

TABLE II

| Example Number | R12 | LCMS[1] (M + H) | min. |
|---|---|---|---|
| 29 | 4-CH₃O—C₆H₄— | 407 | 6.34 |
| 30 | 4-F—C₆H₄— | 395 | 6.75 |
| 31 | 4-Cl—C₆H₄— | 411 | 7.63 |

[1]LCMS conditions: Hewlett Packard 1100 MSD; Primesphere C18 2.0 mm × 150 mm, 5μ; column at 35° C., 2 μL injection; Solvent A: 0.1% HCOOH/water; Solvent B: 0.1% HCOOH/acetonitrile; Gradient: Time 0 min.: 0% B; 8.5 min.: 100% B; 8.6 min: 0% B; Equilibration: 4 min, 20% B; Flow rate 0.5 mL/min; Detection: 254 nm DAD; API-ES Scanning Mode Positive 100–1000; Fragmentor 80 mV.

EXAMPLE 32

Preparation of N-[2-({[(1R)-1-Phenylethyl]amino}methyl)-3,4-dihydro-2H-chromen-7-yl]-2,1,3-benzoxadiazole-4-sulfonamide

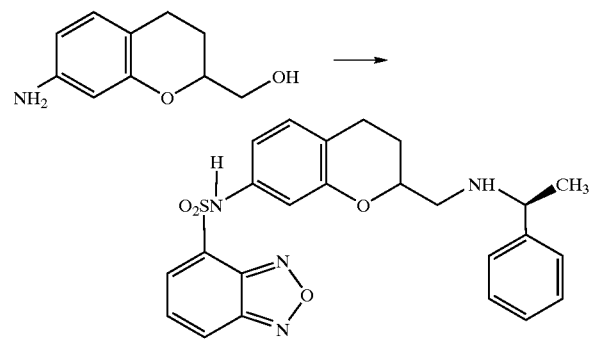

A solution of (7-amino-3,4-dihydro-2H-chromen-2-yl)methanol (28.6 mg, 160 μmol) in pyridine is treated with 2,1,3-benzoxadiazole-4-sulfonyl chloride (39 mg, 180 μmol) at ambient temperatures, stirred for 1 h, treated with phenylsulfonyl chloride (23 μL, 180 μmol) stirred for an additional hour at ambient temperatures, treated with (1R)-1-phenyl-1-ethanamine (1.6 mmol, 206 μL), heated to 100° C. for 2 h, cooled to room temperature, diluted with water and extracted with ethyl acetate. The extracts are combined, dried over $Na_2SO_4$ and concentrated in vacuo. The resultant residue is purified by reverse phase preparative HPLC to give the title product, M+H 465, retention time 3.89 min.

EXAMPLES 33–34

Preparation of [(IR)-1-(Phenethylaminomethyl)chroman-7-yl]arylsulfonamide

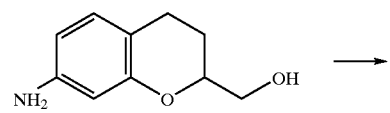

19

-continued

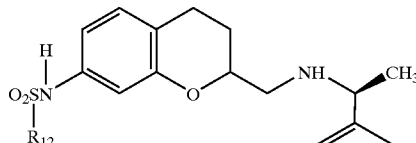

Using essentially the same procedure described in Example 32 hereinabove and substituting the appropriate arylsulfonyl chloride, the compounds shown in Table III are obtained and identified by mass spectral and HPLC analyses (LCMS).

TABLE III

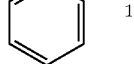

| Example Number | R12 | LCMS[1] (M + H) | min. |
|---|---|---|---|
| 33 | 6-chloroimidazol[2,1-b][1,3]thiazol-5-yl | 503 | 3.88 |
| 34 | 5-bromo-2-thienyl | 509 | 4.26 |
| 35 | 2-(acetylamino)-4-methyl-1,3-thiazol-5-yl | 501 | 3.43 |
| 36 | 5-chloro-3-methyl-1-benzothien-2-yl | 527 | 4.86 |
| 37 | 4-methylphenyl | 437 | 2.07 |
| 38 | 4-chlorophenyl | 457 | 2.06 |
| 39 | 4-methoxyphenyl | 453 | 2.14 |
| 40 | 4-trifluoromethoxyphenyl | 507 | 2.21 |
| 41 | 1-naphthyl | 473 | 2.16 |
| 42 | 5-chlorothien-2-yl | 463 | 2.14 |
| 43 | 4-trifluoromethylphenyl | 491 | 2.20 |
| 44 | 4-aminophenyl | — | — |

[1]LCMS conditions: Hewlett Packard 1100 MSD; Primesphere C18 2.0 mm × 150 mm, 5μ; column at 35° C., 2 μL injection; Solvent A: 0.1% HCOOH/water; Solvent B: 0.1% HCOOH/acetonitrile; Gradient: Time 0 min.: 0% B; 8.5 min.: 100% B; 8.6 min: 0% B; Equilibration: 4 min, 20% B; Flow rate 0.5 mL/min; Detection: 254 nm DAD; API-ES Scanning Mode Positive 100–1000; Fragmentor 80 mV.

20

EXAMPLE 45

Preparation of N-[(2R)-2-({[(1R)-1-Phenylethyl]amino}methyl)-3,4-dihydro-2H-chromen-7-yl-phenylsulfonamide [A] and N[(2S)-2-({[(1R)-1-Phenylethyl]amino}methyl)-3,4-dihydro-2H-chromen-7-yl]phenylsulfonamide [B]

A solution of {7-[(phenylsulfonyl)amino]-3,4-dihydro-2H-chromen-2-yl}methyl benzenesulfonate (0.64 g, 1.3 mmol) and (1R)-1-phenyl-1-ethanamine (1.0 mL, 7.8 mmol) in pyridine is stirred at 100° C. for 1 h, cooled to ambient temperatures, diluted with water and extracted with dichloromethane. The extracts are combined, washed with brine, dried over MgSO₄ and concentrated in vacuo to afford the free base as a mixture of two diastereomers. Separation of the diastereomers by flash chromatography (silica gel, 1:1 ethyl acetate:chloroform) affords the title compound [A] (78 mg, 28% yield) as a clear oil, M+H 423 and the title compound [B] (73 mg, 27% yield) as a clear oil, M+H 423.

EXAMPLE 46

Preparation of N-[(2R)-2-({[(1R)-1-phenylethyl]amino}-methyl)-3,4-dihydro-2H-chromen-7-yl)naphthalene-1-sulfonamide Hydrochloride [A] and N-[(2S)-2({[(1R)-1-phenylethyl]amino}methyl)-3,4-dihydro-2H-chromen-7-yl]naphthalene-1-sulfonamide Hydrochloride [B]

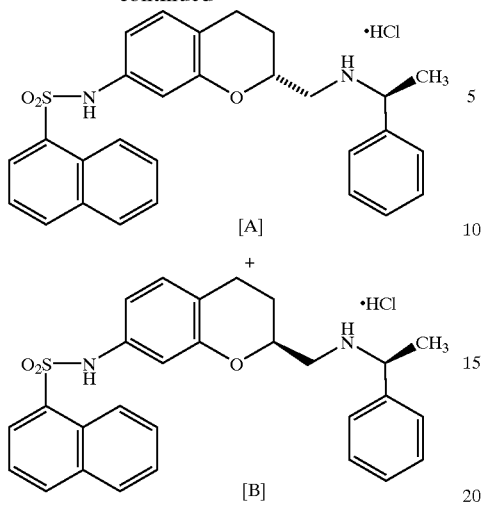

[A]

+

[B]

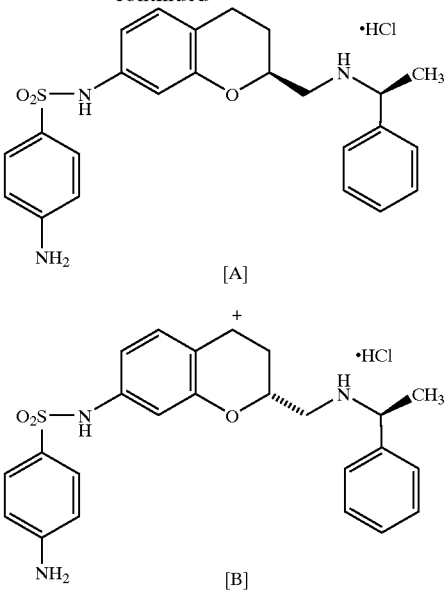

[A]

+

[B]

A solution of (7-amino-3,4-dihydro-2H-chromen-2-yl)methanol (3.1 g; 14 mmol) and pyridine (5.7 mL; 70 mmol) in dichloroethane is treated with 1-naphthalene-sulfonyl chloride (7.1 mL; 15.4 mmol) at ambient temperature for 2 h, treated with pyridine (5.7 mL; 70 mmol) and benzenesulfonyl chloride (7.1 mL; 56 mmol), stirred at 60° C. for 2 h, poured into dilute aqueous HCl and extracted with ethyl acetate. The extracts are combined, washed successively with dilute aqueous HCl, saturated aqueous sodium bicarbonate and brine, dried over $MgSO_4$ and concentrated in vacuo. The resultant oily residue is treated with (1R)-1-phenyl-1-ethanamine, stirred at 100° C. for 2 h, cooled to ambient temperature and partitioned between water and dichloromethane. The organic phase is separated, washed with brine, dried over $Na_2SO_4$ and concentrated in vacuo to afford the free base as a mixture of two diastereomers. Separation of the diastereomers was achieved by preparative chiral HPLC on Chiralpak AS (25×2 cm), 1:1 hexane:ethanol, 12 mL/min to afford the free base of the title compound [A] (2.03 g; 61% yield) as a clear oil and the free base of the title compound [B] (1.87 g; 56.6% yield) as a clear oil. Treatment of each sample with an ethereal solution of hydrogen chloride afforded the title hydrochloride salt [A] as an off-white amorphous powder, mp 230° C. dec, M+H 473 and the title hydrochloride salt [B] as an off-white amorphous powder, mp 240° C. dec, M+H 473.

EXAMPLE 47

Preparation of 4-Amino-N-[(2R)-2-({[(1R)-1-phenylethyl]amino}methyl)-3,4-dihydro-2H-chromen-7-yl]benzenesulfonamide Hydrochloride [A] and 4-Amino-N-[(2S)-2-({[(1R)-1-phenylethyl]amino}methyl)-3,4-dihydro-2H-chromen-7-yl]benezenesulfonamide Hydrochloride [B]

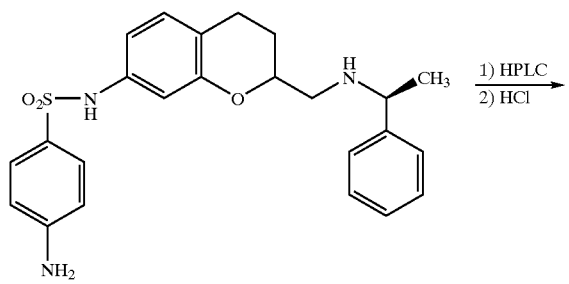

1) HPLC
2) HCl

Using essentially the same separation and hydrochloride salt formation procedures as described in Example 46 hereinabove and employing the racemic compound of Example 44, the title product [A] is obtained as an off-white amorphous powder, mp 208° C., M+H 438 and title product [B] as an off-white amorphous powder, 210° C., M+H 438.

EXAMPLE 48

Preparation of Ethyl 7-(Formylamino)chroman-2-carboxylate

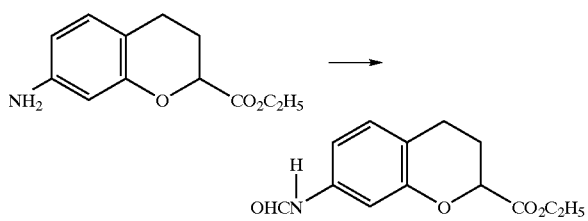

Mixed anhydride is prepared by stirring 1.25 equivalents of formic acid and 1 equivalent of acetic anhydride at 60° C. for 2 h. A solution of ethyl 7-amino-2-chromancarboxylate (1.25 g; 5.6 mmol) in THF is treated with triethylamine (0.78 mL; 5.6 mmol) and the previously prepared mixed anhydride (1.6 mL), stirred at ambient temperature for 1 h, poured into a saturated aqueous solution of sodium bicarbonate and extracted with ethyl ether. The combined extracts are washed with brine, dried over $MgSO_4$ and concentrated in vacuo to afford the title compound as a straw colored oil (1.4 g; 100%), identified by NMR spectral analysis.

EXAMPLE 49

Preparation of [7-(Methylamino)-3,4-dihydro-2H-chromen-2-yl]methanol

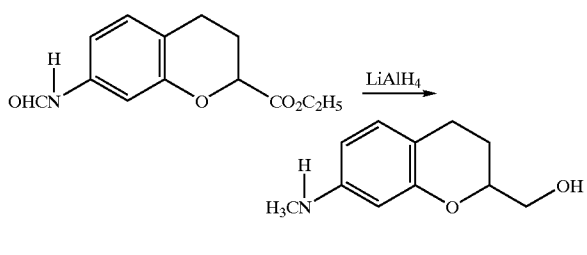

A solution of ethyl 7-(formylamino)chroman-2-carboxylate (1.54 g; 6.00 mmol) in anhydrous THF, under nitrogen, is treated dropwise with a 1 M solution of lithium aluminum hydride in THF (30 mL; 30 mmol), stirred at ambient temperature for 4 h, quenched with a 10% solution of water in THF, with cooling as necessary to maintain room temperature, poured into water and extracted with ethyl acetate. The combined extracts are washed with brine, dried over $MgSO_4$ and concentrated in vacuo to afford the title compound as a straw colored oil (1.13 g; 98% yield), identified by NMR spectral analysis.

EXAMPLE 50

Preparation of 5-Chloro-N-methyl-N-[2-({[(1R)-1-phenylethyl]amino}methyl)-3,4-dihydro-2H-chromen-7-yl)thiophene-2-sulfonamide Hydrochloride

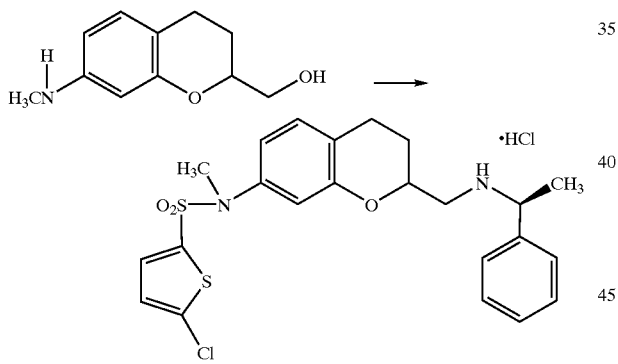

A solution of [7-(methylamino)-3,4-dihydro-2H-chromen-2-yl]methanol (386 mg; 2.00 mmol) and pyridine (0.8 mL; 10 mmol) in dichloroethane is treated with 5-chlorothiophene-2-sulfonyl chloride (477 mg, 2.2 mmol), stirred at ambient temperature for 1 h, treated with pyridine (0.8 mL; 10 mmol) and benzenesulfonyl chloride (1.0 mL; 8 mmol), heated at 60° C. with stirring for 2 h, poured into water and extracted with ethyl ether. The combined extracts are washed successively with dilute aqueous HCl and saturated aqueous solution of sodium bicarbonate, dried over $MgSO_4$ and concentrated in vacuo. The resultant residue is treated with (1R)-1-phenyl-1-ethanamine (2.6 mL; 20 mmol) at 100° C. with stirring for 2 h, cooled to ambient temperature, poured into water and extracted with ethyl ether. The combined extracts are washed with brine, dried over $MgSO_4$ and concentrated in vacuo. The resultant residue is purified by column chromatography (silica gel, 1% methanol in methylene chloride) to afford the free base of the title product as a clear oil (525 mg, 55% yield). Treatment with an ethereal solution of HCl gives the title product as a white crystalline powder, mp 236° C., identified by NMR and mass spectral analyses.

EXAMPLES 51–56

Preparation of N-[2-({[(1R)-1-phenethyl]amino}methyl)-3,4-dihydro-2H-chromen-7-yl]arylsulfonamide HCl

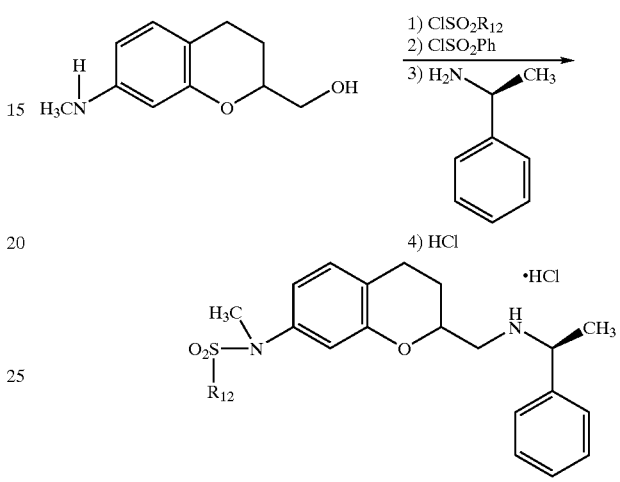

Using essentially the same procedure described in Example 50 hereinabove and employing the appropriate arylsulfonyl chloride, the compounds shown in Table IV are obtained and identified by NMR and mass spectral analyses.

TABLE IV

| Example Number | R12 | mp ° C. |
|---|---|---|
| 51 | 2-bromophenyl | 199–201 |
| 52 | 4-fluorophenyl | 208–210 |
| 53 | 4-chlorophenyl | 198–201 |
| 54 | 3,4-dimethoxyphenyl | 229–230 |
| 55 | 1-naphthyl | 245–246 |
| 56 | 4-aminophenyl | 200° dec |

EXAMPLE 57

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table V, below.

TABLE V

| Test Compound (Ex. No.) | 5-HT6 Binding Ki (nM) |
|---|---|
| 5 | 5 |
| 6 | 4 |
| 7 | 2 |
| 8 | 2 |
| 9 | 2 |
| 10 | 1 |
| 11 | 2 |
| 12 | 5 |
| 13 | 7 |
| 14 | 10 |
| 15 | 17 |
| 16 | 5 |
| 17 | 84 |
| 18 | 41 |
| 19 | 16 |
| 20 | 6 |
| 21 | 8 |
| 22 | 3 |
| 23 | 35 |
| 24 | 72 |
| 25 | 26 |
| 26 | 9 |
| 27 | 7 |
| 28 | 5 |
| 29 | 39 |
| 30 | 49 |
| 31 | 11 |
| 32 | 5 |
| 33 | 3 |
| 34 | 5 |
| 35 | 7 |
| 36 | 45 |
| 37 | 16 |
| 38 | 5 |
| 39 | 10 |
| 40 | 11 |
| 41 | 4 |
| 42 | 2 |
| 43 | 6 |
| 44 | 1 |
| 45A | 1 |
| 45B | 17 |
| 46A | 37 |
| 46B | 2 |
| 49A | 1 |
| 49B | 11 |
| 50 | 1 |
| 51 | 3 |
| 52 | 7 |
| 53 | 5 |
| 54 | 11 |
| 55 | 4 |
| 56 | 4 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention have a high degree of affinity for the 5-HT6 receptor.

What is claimed is:

1. A compound of formula I

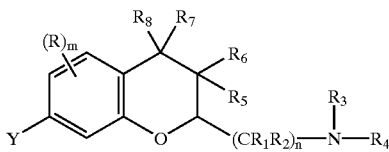

(I)

wherein

Y is $SO_2NR_9R_{10}$ or $NR_{11}ZR_{12}$;

Z is $SO_2$, CONH or CSNH;

R is halogen, CN, $OR_{13}$, $CO_2R_{14}$, $CONR_{15}R_{16}$, $SO_xR_{17}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_1$, $R_2$, $R_5$, $R_6$, $R_7$, $R_8$ and $R_{11}$ are each independently H or an optionally substituted $C_1$–$C_6$alkyl group;

$R_3$ and $R_4$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1$–$C_6$alky or aryl group then $R_3$ and $R_4$ must be other than an optionally substituted $C_3$–$C_6$cycloalkyl or cycloheteroalkyl group;

m is 0 or an integer of 1, 2 or 3;

n is an integer of 1, 2, 3 or 4;

x is 0 or an integer of 1 or 2;

$R_9$ and $R_{10}$ are each independently H or a $C_1$–$C_6$alkyl, aryl or heteroaryl group each optionally substituted;

$R_{12}$ and $R_{17}$ are each independently a $C_1$–$C_6$alkyl, aryl or heteroaryl group each optionally substituted;

$R_{13}$ is H, $CO_2R_{18}$ or a $C_1$–$C_6$alkyl, $C_2$–$C_6$alkenyl, $C_2$–$C_6$alkynyl, aryl or heteroaryl group each optionally substituted;

$R_{14}$ and $R_{18}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_{15}$ and $R_{16}$ are each independently H or an optionally substituted $C_1$–$C_6$alkyl group; or the stereoisomers thereof or a pharmaceutically acceptable salt thereof.

2. The compound according to claim 1 wherein Z is $SO_2$.

3. The compound according to claim 1 wherein $R_{10}$ and $R_{12}$ are each independently an aryl or heteroaryl group each optionally substituted.

4. The compound according to claim 2 wherein n is 1 and m is 0.

5. The compound according to claim 4 wherein Y is $NR_{11}ZR_{12}$.

6. The compound according to claim 5 wherein $R_{12}$ is an aryl or heteroaryl group each optionally substituted.

7. The compound according to claim 6 wherein $R_3$ is H and $R_4$ is a $C_1$–$C_5$alkyl group optionally substituted with hydroxy group or a cycloheteroalkyl, aryl or heteroaryl group each optionally substituted.

8. The compound according to claim 7 wherein $R_5$, $R_6$, $R_7$ and $R_8$ are H.

9. The compound according to claim 8 selected from the group consisting of:

N-{2-[(3-Hydroxy-propylamino)-methyl]-chroman-7-yl}-benzenesulfonamide;

N-(2-{[(3-methoxybenzyl)amino]methyl}-3,4-dihydro-2H-chromen-7-yl)benzenesulfonamide;

N-(2-{[(3-butoxypropyl)amino]methyl}-3,4-dihydro-2H-chromen-7-yl)benzenesulfonamide;

N-{2-[(benzylamino)methyl]-3,4-dihydro-2H-chromen-7-yl}benzenesulfonamide;

N-(2-{[(3-phenoxypropyl)amino]methyl}-3,4-dihydro-2H-chromen-7-yl)benzenesulfonamide;

N-[2-({[(1R)-1-phenylethyl]amino}methyl)-3,4-dihydro-2H-chromen-7-yl]benzenesulfonamide;

N-(2-{[(1,3-benzodioxol-5-ylmethyl)amino]methyl}-3,4-dihydro-2H-chromen-7-yl)benzenesulfonamide;

N-(2-{[(pyridin-3-ylmethyl)amino]methyl}-3,4-dihydro-2H-chromen-7-yl)benzenesulfonamide;

N-{2-[(2,3-dihydro-1H-inden-1-ylamino)methyl]-3,4-dihydro-2H-chromen-7-yl}benzenesulfonamide;

N-[2-({[(1S)-1-phenylethyl]amino}methyl)-3,4-dihydro-2H-chromen-7-yl]benzenesulfonamide;

N-(2-{[(pyridin-4-ylmethyl)amino]methyl}-3,4-dihydro-2H-chromen-7-yl)benzenesulfonamide;

N-[2-({[(1R)-2-hydroxy-1-phenylethyl]amino}methyl)-3,4-dihydro-2H-chromen-7-yl]benzenesulfonamide;

N-(2-{[(1,2-diphenylethyl)amino]methyl}-3,4-dihydro-2H-chromen-7-yl)benzenesulfonamide;

N-(2-{[(2-hydroxy-1,1-dimethylethyl)amino]methyl}-3,4-dihydro-2H-chromen-7-yl)benzenesulfonamide;

N-{2-[(isopropylamino)methyl]-3,4-dihydro-2H-chromen-7-yl}benzenesulfonamide;

N-(2-{[(1-methyl-3-phenylpropyl)amino]methyl}-3,4-dihydro-2H-chromen-7-yl)benzenesulfonamide;

N-(2-{[(1,5-dimethylhexyl)amino]methyl}-3,4-dihydro-2H-chromen-7-yl)benzenesulfonamide;

N-[2-({[(1R)-1-(hydroxymethyl)-3-methylbutyl]amino}methyl)-3,4-dihydro-2H-chromen-7yl]benzenesulfonamide;

N-(2-{[2-(2-hydroxyethyl)piperidin-1-yl]methyl}-3,4-dihydro-2H-chromen-7-yl)benzenesulfonamide;

N-{2-[(2,6-dimethylpiperidin-1-yl)methyl]-3,4-dihydro-2H-chromen-7-yl}benzenesulfonamide;

N-[2-(morpholin-4-ylmethyl)-3,4-dihydro-2H-chromen-7-yl]benzenesulfonamide;

N-[2-(thiomorpholin-4-ylmethyl)-3,4-dihydro-2H-chromen-7-yl]benzenesulfonamide;

N-[2-({[(1R)-1-cyclohexylethyl]amino}methyl)-3,4-dihydro-2H-chromen-7-yl]benzenesulfonamide;

N-(2-{[(3-hydroxypropyl)amino]methyl}-3,4-dihydro-2H-chromen-7-yl)naphthalene-2-sulfonamide;

N-(2-{[(3-hydroxypropyl)amino]methyl}-3,4-dihydro-2H-chromen-7-yl)-4-methoxybenzenesulfonamide;

4-fluoro-N-(2-{[(3-hydroxypropyl)amino]methyl}-3,4-dihydro-2H-chromen-7-yl)benzenesulfonamide;

4-chloro-N-(2-{[(3-hydroxypropyl)amino]methyl}-3,4-dihydro-2H-chromen-7-yl)benzenesulfonamide;

N-[2-({[(1R)-1-phenylethyl]amino}methyl)-3,4-dihydro-2H-chromen-7-yl]-2,1,3-benzoxadiazole-4-sulfonamide;

6-chloro-N-[2-({[(1R)-1-phenylethyl]amino}methyl)-3,4-dihydro-2H-chromen-7-yl]imidazo[2,1-b][1,3]thiazole-5-sulfonamide;

5-bromo-N-[2-({[(1R)-1-phenylethyl]amino}methyl)-3,4-dihydro-2H-chromen-7-yl]-2-thiophenesulfonamide;
N-[4-methyl-5-({[2-({[(1R)-1-phenylethyl]amino}methyl)-3,4-dihydro-2H-chromen-7-yl]amino}sulfonyl)-1,3-thiazol-2-yl]acetamide;
5-chloro-3-methyl-N-[2-({[(1R)-1-phenylethyl]amino}methyl)-3,4-dihydro-2H-chromen-7-yl]-1-benzothiophene-2-sulfonamide;
N-[(2R)-2-({[(1R)-1-phenylethyl]amino}methyl)-3,4-dihydro-2H-chromen-7-yl]benzenesulfonamide;
N-[(2S)-2-({[(1R)-1-phenylethyl]amino}methyl)-3,4-dihydro-2H-chromen-7-yl]benzenesulfonamide;
4-methyl-N-[2-({[(1R)-1-phenylethyl]amino}methyl)-3,4-dihydro-2H-chromen-7-yl]benzenesulfonamide;
4-chloro-N-[2-({[(1R)-1-phenylethyl]amino}methyl)-3,4-dihydro-2H-chromen-7-yl]benzenesulfonamide;
4-methoxy-N-[2-({[(1R)-1-phenylethyl]amino}methyl)-3,4-dihydro-2H-chromen-7-yl]benzenesulfonamide;
N-[2-({[(1R)-1-phenylethyl]amino}methyl)-3,4-dihydro-2H-chromen-7-yl]-4-(trifluoromethoxy)benzenesulfonamide;
N-[2-({[(1R)-1-phenylethyl]amino}methyl)-3,4-dihydro-2H-chromen-7-yl]naphthalene-1-sulfonamide;
5-chloro-N-[2-({[(1R)-1-phenylethyl]amino}methyl)-3,4-dihydro-2H-chromen-7-yl]thiophene-2-sulfonamide;
N-[2-({[(1R)-1-phenylethyl]amino}methyl)-3,4-dihydro-2H-chromen-7-yl]-4-(trifluoromethyl)benzenesulfonamide;
5-chloro-N-methyl-N-[2-({[(1R)-1-phenylethyl]amino}methyl)-3,4-dihydro-2H-chromen-7-yl]thiophene-2-sulfonamide;
4-amino-N-[2-({[(1R)-1-phenylethyl]amino}methyl)-3,4-dihydro-2H-chromen-7-yl]benzenesulfonamide;
2-bromo-N-methyl-N-[2-({[(1R)-1-phenylethyl]amino}methyl)-3,4-dihydro-2H-chromen-7-yl]benzenesulfonamide;
4-fluoro-N-methyl-N-[2-({[(1R)-1-phenylethyl]amino}methyl)-3,4-dihydro-2H-chromen-7-yl]benzenesulfonamide;
4-chloro-N-methyl-N-[2-({[(1R)-1-phenylethyl]amino}methyl)-3,4-dihydro-2H-chromen-7-yl]benzenesulfonamide;
3,4-dimethoxy-N-methyl-N-[2-({[(1R)-1-phenylethyl]amino}methyl)-3,4-dihydro-2H-chromen-7-yl]benzenesulfonamide;
N-methyl-N-[2-({[(1R)-1-phenylethyl]amino}methyl)-3,4-dihydro-2H-chromen-7-yl]naphthalene-1-sulfonamide;
4-amino-N-methyl-N-[2-({[(1R)-1-phenylethyl]amino}methyl)-3,4-dihydro-2H-chromen-7-yl]benzenesulfonamide;
N-[(2R)-2-({[(1R)-1-phenylethyl]amino}methyl)-3,4-dihydro-2H-chromen-7-yl]naphthalene-1-sulfonamide;
N-[(2S)-2-({[(1R)-1-phenylethyl]amino}methyl)-3,4-dihydro-2H-chromen-7-yl]naphthalene-1-sulfonamide;
4-amino-N-[(2R)-2-({[(1R)-1-phenylethyl]amino}methyl)-3,4-dihydro-2H-chromen-7-yl]benzenesulfonamide;
4-amino-N-[(2S)-2-({[(1R)-1-phenylethyl]amino}methyl)-3,4-dihydro-2H-chromen-7-yl]benzenesulfonamide;
the stereoisomers thereof; and
the pharmaceutically acceptable salts thereof.

10. A method for the treatment of a disorder of the central nervous system related to or affected by the 5-HT6 receptor in a patient in need thereof which comprises providing to said patient a therapeutically effective amount of a compound of formula I

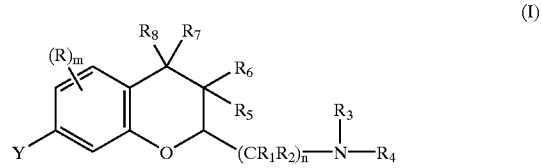

wherein
Y is $SO_2NR_9R_{10}$ or $NR_{11}ZR_{12}$;
Z is $SO_2$, CONH or CSNH;
R is halogen, CN, $OR_{13}$, $CO_2R_{14}$, $CONR_{15}R_{16}$, $SO_xR_{17}$ or a $C_1-C_6$alkyl, $C_2-C_6$alkenyl, $C_2-C_6$alkynyl, $C_3-C_6$cycloalkyl, cycloheteroalkyl, phenyl or heteroaryl group each optionally substituted;
$R_1$, $R_2$, $R_5$, $R_6$, $R_7$, $R_8$ and $R_{11}$ are each independently H or an optionally substituted $C_1-C_6$alkyl group;
$R_3$ and $R_4$ are each independently H or a $C_1-C_6$alkyl, $C_3-C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1-C_6$alky or aryl group then $R_3$ and $R_4$ must be other than an optionally substituted $C_3-C_6$cycloalkyl or cycloheteroalkyl group;
m is 0 or an integer of 1, 2 or 3;
n is an integer of 1, 2, 3 or 4;
x is 0 or an integer of 1 or 2;
$R_9$ and $R_{10}$ are each independently H or a $C_1-C_6$alkyl, aryl or heteroaryl group each optionally substituted;
$R_{12}$ and $R_{17}$ are each independently a $C_1-C_6$alkyl, aryl or heteroaryl group each optionally substituted;
$R_{13}$ is H, $CO_2R_{18}$ or a $C_1-C_6$alkyl, $C_2-C_6$alkenyl, $C_2-C_6$alkynyl, aryl or heteroaryl group each optionally substituted;
$R_{14}$ and $R_{18}$ are each independently H or a $C_1-C_6$alkyl, $C_2-C_6$alkenyl, $C_2-C_6$alkynyl, $C_3-C_6$cycloalkyl, cycloheteroalkyl, aryl or heteroaryl group each optionally substituted; and
$R_{15}$ and $R_{16}$ are each independently H or an optionally substituted $C_1-C_6$alkyl group; or
the stereoisomers thereof or a pharmaceutically acceptable salt thereof.

11. The method according to claim 10 wherein said disorder is a motor disorder, anxiety disorder or cognitive disorder.

12. The method according to claim 10 wherein said disorder is schizophrenia or depression.

13. The method according to claim 11 wherein said disorder is Alzheimer's disease or Parkinson's disease.

14. The method according to claim 11 wherein said disorder is attention deficit disorder.

15. A pharmaceutical composition which comprises a pharmaceutically acceptable carrier and an effective amount of a compound of formula I

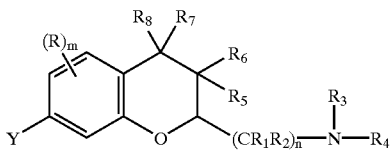

(I)

wherein
Y is $SO_2NR_9R_{10}$ or $NR_{11}ZR_{12}$;
Z is $SO_2$, CONH or CSNH;
R is halogen, CN, $OR_{13}$, $CO_2R_{14}$, $CONR_{15}R_{16}$, $SO_xR_{17}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_1$, $R_2$, $R_5$, $R_6$, $R_7$, $R_8$ and $R_{11}$ are each independently H or an optionally substituted $C_1$–$C_6$alkyl group;
$R_3$ and $R_4$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1$–$C_6$alky or aryl group then $R_3$ and $R_4$ must be other than an optionally substituted $C_3$–$C_6$cycloalkyl or cycloheteroalkyl group;
m is 0 or an integer of 1, 2 or 3;
n is an integer of 1, 2, 3 or 4;
x is 0 or an integer of 1 or 2;
$R_9$ and $R_{10}$ are each independently H or a $C_1$–$C_6$alkyl, aryl or heteroaryl group each optionally substituted;
$R_{12}$ and $R_{17}$ are each independently a $C_1$–$C_6$alkyl, aryl or heteroaryl group each optionally substituted;
$R_{13}$ is H, $CO_2R_{18}$ or a $C_1$–$C_6$alkyl, $C_2$–$C_6$alkenyl, $C_2$–$C_6$alkynyl, aryl or heteroaryl group each optionally substituted;
$R_{14}$ and $R_{18}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and
$R_{15}$ and $R_{16}$ are each independently H or an optionally substituted $C_1$–$C_6$alkyl group; or
the stereoisomers thereof or a pharmaceutically acceptable salt thereof.

16. The composition according to claim 15 having a formula I compound wherein Z is $SO_2$.

17. The composition according to claim 16 having a formula I compound wherein n is 1; m is 0; and $R_{12}$ is an aryl or heteroaryl group each optionally substituted.

18. The composition according to claim 17 having a formula I compound wherein $R_3$ is H and $R_4$ is a $C_1$–$C_6$alkyl group optionally substituted with hydroxy group or a cycloheteroalkyl, aryl or heteroaryl group each optionally substituted.

19. The composition according to claim 18 having a formula I compound selected from the group consisting of:
N-{2-[(3-Hydroxy-propylamino)-methyl]-chroman-7-yl}-benzenesulfonamide;
N-(2-{[(3-methoxybenzyl)amino]methyl}-3,4-dihydro-2H-chromen-7-yl)benzenesulfonamide;
N-(2-{[(3-butoxypropyl)amino]methyl}-3,4-dihydro-2H-chromen-7-yl)benzenesulfonamide;
N-{2-[(benzylamino)methyl]-3,4-dihydro-2H-chromen-7-yl}benzenesulfonamide;
N-(2-{[(3-phenoxypropyl)amino]methyl}-3,4-dihydro-2H-chromen-7-yl)benzenesulfonamide;
N-[2-({[(1R)-1-phenylethyl]amino}methyl)-3,4-dihydro-2H-chromen-7-yl]benzenesulfonamide;
N-(2-{[(1,3-benzodioxol-5-ylmethyl)amino]methyl}-3,4-dihydro-2H-chromen-7-yl)benzenesulfonamide;
N-(2-{[(pyridin-3-ylmethyl)amino]methyl}-3,4-dihydro-2H-chromen-7-yl)benzenesulfonamide;
N-{2-[(2,3-dihydro-1H-inden-1-ylamino)methyl]-3,4-dihydro-2H-chromen-7-yl}benzenesulfonamide;
N-[2-({[(1S)-1-phenylethyl]amino}methyl)-3,4-dihydro-2H-chromen-7-yl]benzenesulfonamide;
N-(2-{[(pyridin-4-ylmethyl)amino]methyl}-3,4-dihydro-2H-chromen-7-yl)benzenesulfonamide;
N-[2-({[(1R)-2-hydroxy-1-phenylethyl]amino}methyl)-3,4-dihydro-2H-chromen-7-yl]benzenesulfonamide;
N-(2-{[(1,2-diphenylethyl)amino]methyl}-3,4-dihydro-2H-chromen-7-yl)benzenesulfonamide;
N-(2-{[(2-hydroxy-1,1-dimethylethyl)amino]methyl}-3,4-dihydro-2H-chromen-7-yl)benzenesulfonamide;
N-{2-[(isopropylamino)methyl]-3,4-dihydro-2H-chromen-7-yl}benzenesulfonamide;
N-(2-{[(1-methyl-3-phenylpropyl)amino]methyl}-3,4-dihydro-2H-chromen-7-yl)benzenesulfonamide;
N-(2-{[(1,5-dimethylhexyl)amino]methyl}-3,4-dihydro-2H-chromen-7-yl)benzenesulfonamide;
N-[2-({[(1R)-1-(hydroxymethyl)-3-methylbutyl]amino}methyl)-3,4-dihydro-2H-chromen-7yl]benzenesulfonamide;
N-(2-{[2-(2-hydroxyethyl)piperidin-1-yl]methyl}-3,4-dihydro-2H-chromen-7-yl)benzenesulfonamide;
N-{2-[(2,6-dimethylpiperidin-1-yl)methyl]-3,4-dihydro-2H-chromen-7-yl}benzenesulfonamide;
N-[2-(morpholin-4-ylmethyl)-3,4-dihydro-2H-chromen-7-yl]benzenesulfonamide;
N-[2-(thiomorpholin-4-ylmethyl)-3,4-dihydro-2H-chromen-7-yl]benzenesulfonamide;
N-[2-({[(1R)-1-cyclohexylethyl]amino}methyl)-3,4-dihydro-2H-chromen-7-yl]benzenesulfonamide;
N-(2-{[(3-hydroxypropyl)amino]methyl}-3,4-dihydro-2H-chromen-7-yl)naphthalene-2-sulfonamide;
N-(2-{[(3-hydroxypropyl)amino]methyl}-3,4-dihydro-2H-chromen-7-yl)-4-methoxybenzenesulfonamide;
4-fluoro-N-(2-{[(3-hydroxypropyl)amino]methyl}-3,4-dihydro-2H-chromen-7-yl)benzenesulfonamide;
4-chloro-N-(2-{[(3-hydroxypropyl)amino]methyl}-3,4-dihydro-2H-chromen-7-yl)benzenesulfonamide;
N-[2-({[(1R)-1-phenylethyl]amino}methyl)-3,4-dihydro-2H-chromen-7-yl]-2,1,3-benzoxadiazole-4-sulfonamide;
6-chloro-N-[2-({[(1R)-1-phenylethyl]amino}methyl)-3,4-dihydro-2H-chromen-7-yl]imidazo[2,1-b][1,3]thiazole-5-sulfonamide;
5-bromo-N-[2-({[(1R)-1-phenylethyl]amino}methyl)-3,4-dihydro-2H-chromen-7-yl]-2-thiophenesulfonamide;

N-[4-methyl-5-({[2-({[(1R)-1-phenylethyl]amino}methyl)-3,4-dihydro-2H-chromen-7-yl]amino}sulfonyl)-1,3-thiazol-2-yl]acetamide;

5-chloro-3-methyl-N-[2-({[(1R)-1-phenylethyl]amino}methyl)-3,4-dihydro-2H-chromen-7-yl]-1-benzothiophene-2-sulfonamide;

N-[(2R)-2-({[(1R)-1-phenylethyl]amino}methyl)-3,4-dihydro-2H-chromen-7-yl]benzenesulfonamide;

N-[(2S)-2-({[(1R)-1-phenylethyl]amino}methyl)-3,4-dihydro-2H-chromen-7-yl]benzenesulfonamide;

4-methyl-N-[2-({[(1R)-1-phenylethyl]amino}methyl)-3,4-dihydro-2H-chromen-7-yl]benzenesulfonamide;

4-chloro-N-[2-({[(1R)-1-phenylethyl]amino}methyl)-3,4-dihydro-2H-chromen-7-yl]benzenesulfonamide;

4-methoxy-N-[2-({[(1R)-1-phenylethyl]amino}methyl)-3,4-dihydro-2H-chromen-7-yl]benzenesulfonamide;

N-[2-({[(1R)-1-phenylethyl]amino}methyl)-3,4-dihydro-2H-chromen-7-yl]-4-(trifluoromethoxy)benzenesulfonamide;

N-[2-({[(1R)-1-phenylethyl]amino}methyl)-3,4-dihydro-2H-chromen-7-yl]naphthalene-1-sulfonamide;

5-chloro-N-[2-({[(1R)-1-phenylethyl]amino}methyl)-3,4-dihydro-2H-chromen-7-yl]thiophene-2-sulfonamide;

N-[2-({[(1R)-1-phenylethyl]amino}methyl)-3,4-dihydro-2H-chromen-7-yl]-4-(trifluoromethyl)benzenesulfonamide;

5-chloro-N-methyl-N-[2-({[(1R)-1-phenylethyl]amino}methyl)-3,4-dihydro-2H-chromen-7-yl]thiophene-2-sulfonamide;

4-amino-N-[2-({[(1R)-1-phenylethyl]amino}methyl)-3,4-dihydro-2H-chromen-7-yl]benzenesulfonamide;

2-bromo-N-methyl-N-[2-({[(1R)-1-phenylethyl]amino}methyl)-3,4-dihydro-2H-chromen-7-yl]benzenesulfonamide;

4-fluoro-N-methyl-N-[2-({[(1R)-1-phenylethyl]amino}methyl)-3,4-dihydro-2H-chromen-7-yl]benzenesulfonamide;

4-chloro-N-methyl-N-[2-({[(1R)-1-phenylethyl]amino}methyl)-3,4-dihydro-2H-chromen-7-yl]benzenesulfonamide;

3,4-dimethoxy-N-methyl-N-[2-({[(1R)-1-phenylethyl]amino}methyl)-3,4-dihydro-2H-chromen-7-yl]benzenesulfonamide;

N-methyl-N-[2-({[(1R)-1-phenylethyl]amino}methyl)-3,4-dihydro-2H-chromen-7-yl]naphthalene-1-sulfonamide;

4-amino-N-methyl-N-[2-({[(1R)-1-phenylethyl]amino}methyl)-3,4-dihydro-2H-chromen-7-yl]benzenesulfonamide;

N-[(2R)-2-({[(1R)-1-phenylethyl]amino}methyl)-3,4-dihydro-2H-chromen-7-yl]naphthalene-1-sulfonamide;

N-[(2S)-2-({[(1R)-1-phenylethyl]amino}methyl)-3,4-dihydro-2H-chromen-7-yl]naphthalene-1-sulfonamide;

4-amino-N-[(2R)-2-({[(1R)-1-phenylethyl]amino}methyl)-3,4-dihydro-2H-chromen-7-yl]benzenesulfonamide;

4-amino-N-[(2S)-2-({[(1R)-1-phenylethyl]amino}methyl)-3,4-dihydro-2H-chromen-7-yl]benzenesulfonamide;

the stereoisomers thereof; and
the pharmaceutically acceptable salts thereof.

20. A process for the preparation of a compound of formula I

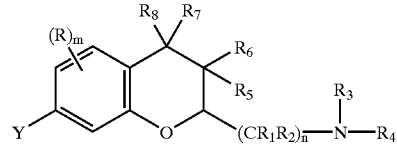

wherein

Y is $SO_2NR_9R_{10}$ or $NR_{11}ZR_{12}$;

Z is $SO_2$, CONH or CSNH;

R is halogen, CN, $OR_{13}$, $CO_2R_{16}$, $CONR_{15}R_{16}$, $SO_xR_{17}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_1$, $R_2$, $R_5$, $R_6$, $R_7$, $R_8$ and $R_{11}$ are each independently H or an optionally substituted $C_1$–$C_6$alkyl group;

$R_3$ and $R_4$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when $R_{12}$ is an optionally substituted $C_1$–$C_6$alky or aryl group then $R_3$ and $R_4$ must be other than an optionally substituted $C_3$–$C_6$cycloalkyl or cycloheteroalkyl group;

m is 0 or an integer of 1, 2 or 3;

n is an integer of 1, 2, 3 or 4;

x is 0 or an integer of 1 or 2;

$R_9$ and $R_{10}$ are each independently H or a $C_1$–$C_6$alkyl, aryl or heteroaryl group each optionally substituted;

$R_{12}$ and $R_{17}$ are each independently a $C_1$–$C_6$alkyl, aryl or heteroaryl group each optionally substituted;

$R_{13}$ is H, $CO_2R_{18}$ or a $C_1$–$C_6$alkyl, $C_2$–$C_6$alkenyl, $C_2$–$C_6$alkynyl, aryl or heteroaryl group each optionally substituted;

$R_{14}$ and $R_{18}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_{15}$ and $R_{16}$ are each independently H or an optionally substituted $C_1$–$C_6$alkyl group which process comprises reacting a compound of formula XIII

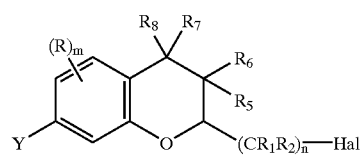

wherein Y, m, n, R, $R_1$, $R_2$, $R_5$, $R_6$, $R_7$ and $R_8$ are as defined above and Hal is Cl, Br or I with an amine, $HNR_3R_4$, at an elevated temperature optionally in the presence of a solvent to give the desired product of formula I.

* * * * *